United States Patent
Zhao et al.

(10) Patent No.: US 6,730,057 B2
(45) Date of Patent: May 4, 2004

(54) FLUSHABLE TAMPON APPLICATORS

(75) Inventors: Jean Jianqun Zhao, Cincinnati, OH (US); Gary Wayne Gilbertson, Liberty Township, OH (US); Andrew Julian Wnuk, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 116 days.

(21) Appl. No.: 09/810,292

(22) Filed: Mar. 16, 2001

(65) Prior Publication Data

US 2003/0036721 A1 Feb. 20, 2003

(51) Int. Cl.[7] .................................................. A61F 13/20
(52) U.S. Cl. ........................... 604/11; 604/364; 604/15; 604/904
(58) Field of Search ................. 604/11–18, 364; 525/56–58, 60, 64, 187, 303

(56) References Cited

U.S. PATENT DOCUMENTS

| | | |
|---|---|---|
| 3,724,462 A | 4/1973 | Hanke |
| 3,882,196 A | 5/1975 | Hanke |
| 3,882,869 A | 5/1975 | Hanke |
| 3,911,917 A | 10/1975 | Hanke |
| 4,233,196 A * | 11/1980 | Sublett ........................ 524/602 |
| 4,372,311 A | 2/1983 | Potts |
| 4,503,098 A | 3/1985 | Potts |
| 4,650,459 A | 3/1987 | Sheldon |
| 4,946,932 A * | 8/1990 | Jenkins ........................ 528/272 |
| 5,002,526 A | 3/1991 | Herring |
| 5,087,650 A * | 2/1992 | Willett ........................ 524/47 |
| 5,310,827 A * | 5/1994 | Komiya et al. ............. 525/439 |
| 5,367,003 A | 11/1994 | Petcavich |
| 5,395,308 A | 3/1995 | Fox et al. |
| 5,496,874 A | 3/1996 | Faass et al. |
| 5,509,913 A | 4/1996 | Yeo |
| 5,644,020 A | 7/1997 | Timmermann et al. |
| 5,738,646 A | 4/1998 | Fox et al. |
| 5,782,794 A | 7/1998 | Assenheimer Downs |
| 5,804,653 A | 9/1998 | Weng |
| 5,916,969 A | 6/1999 | Wang et al. |
| 5,954,683 A | 9/1999 | Downs et al. |
| 6,010,971 A | 1/2000 | Tsai et al. |
| 6,020,425 A | 2/2000 | Wang et al. |
| 6,103,809 A | 8/2000 | Ahmed et al. |
| 6,110,849 A | 8/2000 | Tsai et al. |

FOREIGN PATENT DOCUMENTS

| | | |
|---|---|---|
| CA | 2161059 | 4/1996 |
| EP | 0 613 672 A1 | 9/1994 |
| EP | 0 635 545 A2 | 1/1995 |
| EP | 0 860 471 A1 | 8/1998 |
| GB | 2 340 835 A | 3/2000 |
| JP | 09308105 | 5/1999 |
| JP | 09366175 | 7/1999 |
| WO | WO 96/04338 A1 | 2/1996 |
| WO | WO 98/29493 A1 | 7/1998 |
| WO | WO 98/29506 A1 | 7/1998 |
| WO | WO 99/33921 A1 | 7/1999 |
| WO | WO 00/02955 A1 | 1/2000 |
| WO | WO 00/39211 A2 | 7/2000 |
| WO | WO 00/39218 A2 | 7/2000 |
| ZA | 832776 | 4/1988 |

* cited by examiner

*Primary Examiner*—Kim M. Lewis
*Assistant Examiner*—Jacqueline F Stephens
(74) *Attorney, Agent, or Firm*—Bridget D. Ammons; Kevin C. Johnson

(57) ABSTRACT

Disclosed are flushable tampon applicators which comprise a combination of thermoplastic materials that readily disintegrate in water such as toilet water for improved disposal and reduced environmetal concerns regarding the destruction of these applicators. The flushable tampon applicators comprise a combination of high molecular weight polyethylene oxides, low molecular weight polyethylene glycols, and biodegradable polymers, wherein this combination of water-dispersible and biodegradable thermoplastic polymers provide flushable tampon applicators that are readily disposed of and that are smooth, soft, flexible, and non-sticky or non-slimy to the touch before and during use.

13 Claims, 2 Drawing Sheets

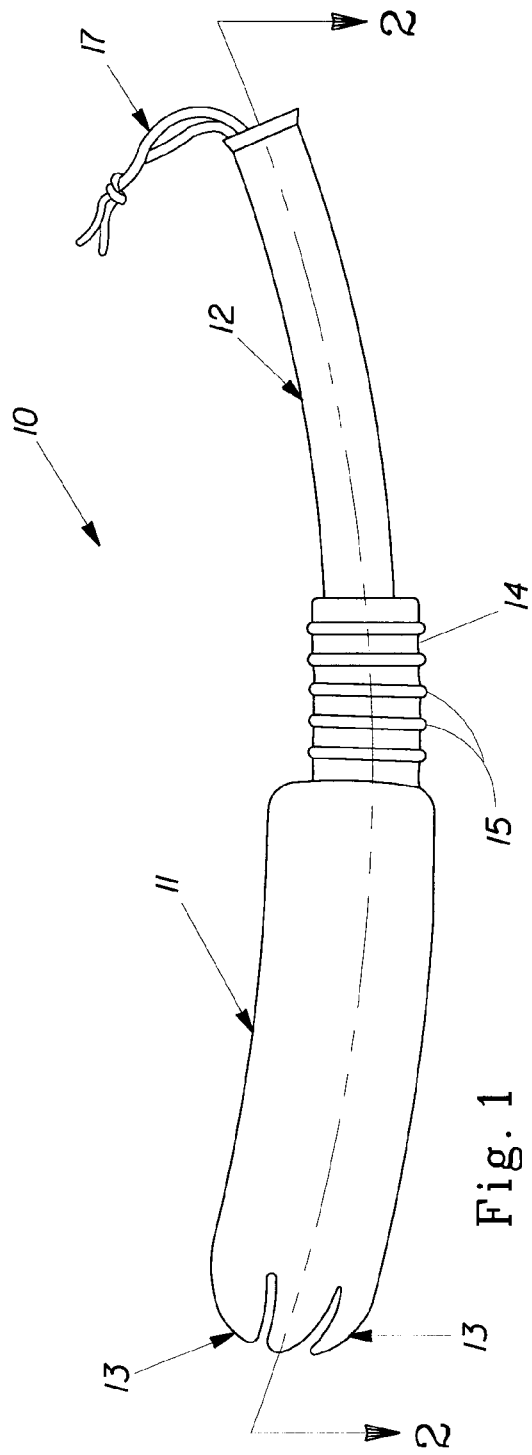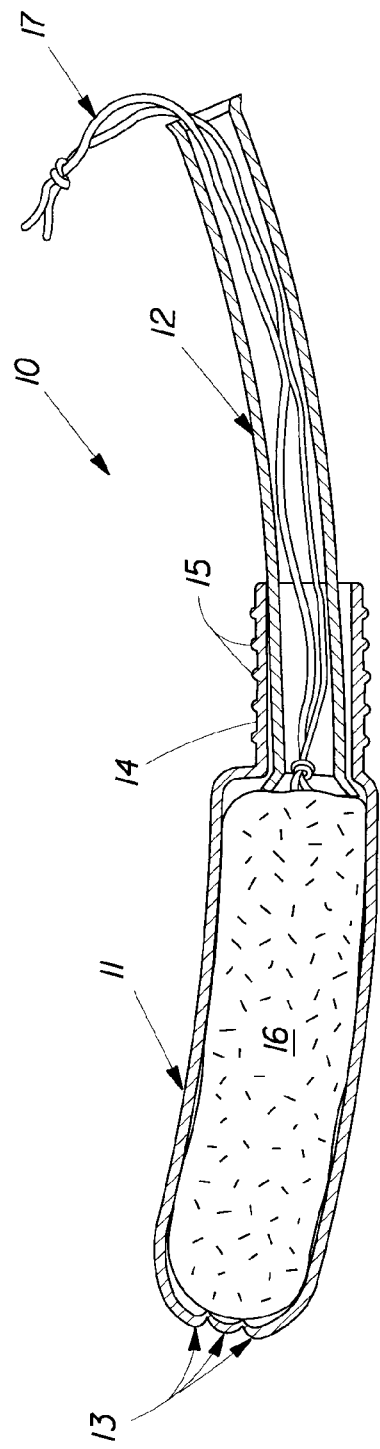

FLUSHABLE TAMPON APPLICATORS

FIELD OF THE INVENTION

The present invention relates to plastic tampon applicators which are readily disposed in a sewage system and/or by biodegradation. In particular, the present invention relates to flushable tampon applicators which are made from thermoplastic materials that are suitable for rapid disposal in a toilet system.

BACKGROUND OF THE INVENTION

Feminine hygiene products such as tampons are commonly used by female consumers. Tampons can be described as a feminine hygiene article that has an absorbent device (i.e., pledget) withheld in a paper or plastic applicator.

Paper and plastic tampon applicators typically comprise an outer tubular member and a plunger for insertion of the pledget, whereby these components of the paper and plastic applicators are generally made from paper, paper coated, and plastic materials which retain their form during use and are shelf-stable under ambient conditions.

In addition to absorbent pledget devices, paper tampon applicator components are suitable for disposal via a sewage system or by biodegradable waste disposal means. Therefore, paper tampon applicators are considered environmentally friendly in that these paper tampon applicators can readily disintegrate in a sewage system and/or can be disposed of through aerobic, anaerobic, and natural degradation processes. However, paper tampon articles are not very popular among females due to some tampon's pledget insertion difficulties associated with the use of a paper tampon applicator.

Certain female consumers prefer plastic tampon applicators because the plastic applicators are made with a grip ring and petal-shaped forward end which facilitate ease of insertion of a tampon's pledget, although plastic tampon applicator components are not easily disposed of as compared to paper applicator components. Most plastic tampon applicators are made from polyethylene-based polymeric materials that are not biodegradable and that do not readily soften or break-up into smaller fragments for decomposition in a sewage system, resulting in increased environmental concerns for the disposal of plastic tampon applicators.

Many efforts to address the environmental concerns of the disposal of plastic tampon applicators include the manufacture of tampon applicators from thermoplastic materials other than polyethylene polymers. Such attempts include tampon applicators made from water-soluble materials, water-dispersible materials, biodegradable materials, photodegradable materials, ultraviolet light degradable materials, or combinations thereof. In particular, one attempt to address the disposal of plastic tampon applicators involves the use of plastic applicators made from biodegradable polymers such as polyvinyl alcohol polymers. It is known that tampon applicators made primarily from polyvinyl alcohol are water-dispersible and biodegradable, however, such applicators have been shown to suffer from issues involving moisture sensitivity, stability, odor, and stickiness.

Other attempts in addressing the disposal of plastic tampon applicators include plastic tampon applicators made from other water-soluble materials such as polyethylene oxide polymers, thermoplastic starch, and hydroxypropyl cellulose; plastic tampon applicators made from combinations of water-soluble and water-insoluble/biodegradable materials such as combinations of polyvinyl alcohol and polycaprolactone, combinations of polyethylene oxide and polycaprolactone, combinations of polyethylene oxide and polyolefins such as polypropylene and polyethylene; and combinations of polyvinyl alcohol and polyethylene oxide polymers.

An example of a plastic tampon applicator constructed from a combination of polyvinyl alcohol and polyethylene oxide is disclosed in U.S. Pat. No. 5,395,308. This plastic tampon applicator is described as being constructed to exhibit accelerated break-up and rapid disintegration in liquid such as water so that the plastic applicator can dissolve over an extended period of time without causing problems in sewage systems such as a waste treatment facility. The slow dissolution rate of these plastic tampon applicators can lead to the clogging of toilet systems and/or drain pipes because of the extended time required for these plastic applicators to initially come in contact with liquid such as toilet water and eventually reach waste disposal means at a waste treatment facility, especially if multiple plastic applicators are suited for disposal.

Therefore, the need exists for the manufacture of plastic tampon applicators made from thermoplastic materials that are flushable and can not only readily lose their structural integrity as for example breaking apart in unrecognizable pieces in a sewage system such as a toilet, but that can readily soften, disperse, disintegrate, and/or dissolve in a toilet for clear passage through the toilet to a municipal waste treatment facility. The tampon applicator components should also be anerobically and/or aerobically biodegradable, as well as provide for a flushable tampon applicator that is not slimy, sticky, or tacky to the touch before and during use.

SUMMARY OF THE INVENTION

The present invention is directed to flushable tampon applicators which comprise (a) from about 1% to about 90% by weight of polyethylene oxides having a weight average molecular weight of from about 65,000 daltons to about 8,000,000 daltons; (b) from about 1% to about 40% by weight of polyethylene glycols having a number average molecular weight of from about 500 daltons to about 20,000 daltons; and (c) from about 9% to about 59% by weight of a biodegradable polymer.

The present invention is also directed to a method of making flushable tampon applicators wherein the method comprises (a) preparing a blended thermoplastic composition comprising (i) from about 1% to about 90% by weight of polyethylene oxides having a weight average molecular weight of from about 65,000 daltons to about 8,000,000 daltons; (ii) from about 1% to about 40% by weight of polyethylene glycols having a number average molecular weight of from about 500 daltons to about 20,000 daltons; and (iii) from about 9% to about 59% by weight of a biodegradable polymer and (b) injection molding the blended thermoplastic composition into molded thermoplastic components used to construct the flushable tampon applicator.

It has been found that flushable tampon applicators can be made from a combination of thermoplastic materials, especially a blend of high molecular weight polyethylene oxides, low molecular weight polyethylene glycols, and biodegradable polymers such as aliphatic polyesteramides, to result in flushable tampon applicators that readily disintegrate in a septic tank such as a toilet and are easily disposed of with minimal or no environmental issues. The flushable tampon applicators of the present invention comprise a combination of water-dispersible and biodegradable thermoplastic polymers which provide for improved disposal properties of the applicators. These applicators are capable of being flushed down a toilet or any other sewage system without causing drainage problems such as clogging, and are capable of biodegradation disposal using commonly employed biodegradation means.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1 is a perspective representation of a flushable tampon applicator (10) of the present invention made from a blend of thermoplastic materials. The flushable tampon applicator comprise a thermoplastic outer tubular member (11) and a thermoplastic inner tubular member or plunger (12). The outer tubular member (11) can be any known or otherwise effective thermoplastic, one-piece, hollow cylindrical body that has a plurality of flexible petal tips (13) extending from and disposed on the front end of the outer tube. The outer tubular member (11) functions to contain or house an absorbent device such as a pledget (not shown), and typically has a finger grip ring (14) formed on the opposite end of the outer tube wherein the finger grip ring has one or more ribs or protusions (15) on its exterior to provide a gripping surface to assist a user in holding the flushable tampon applicator (10). The finger grip portion of the outer tubular member (11) can be of other configurations such as gripping rings having score lines, ridges, dimples, one or more flat surfaces, a roughed surface, and so forth.

Figure 3:
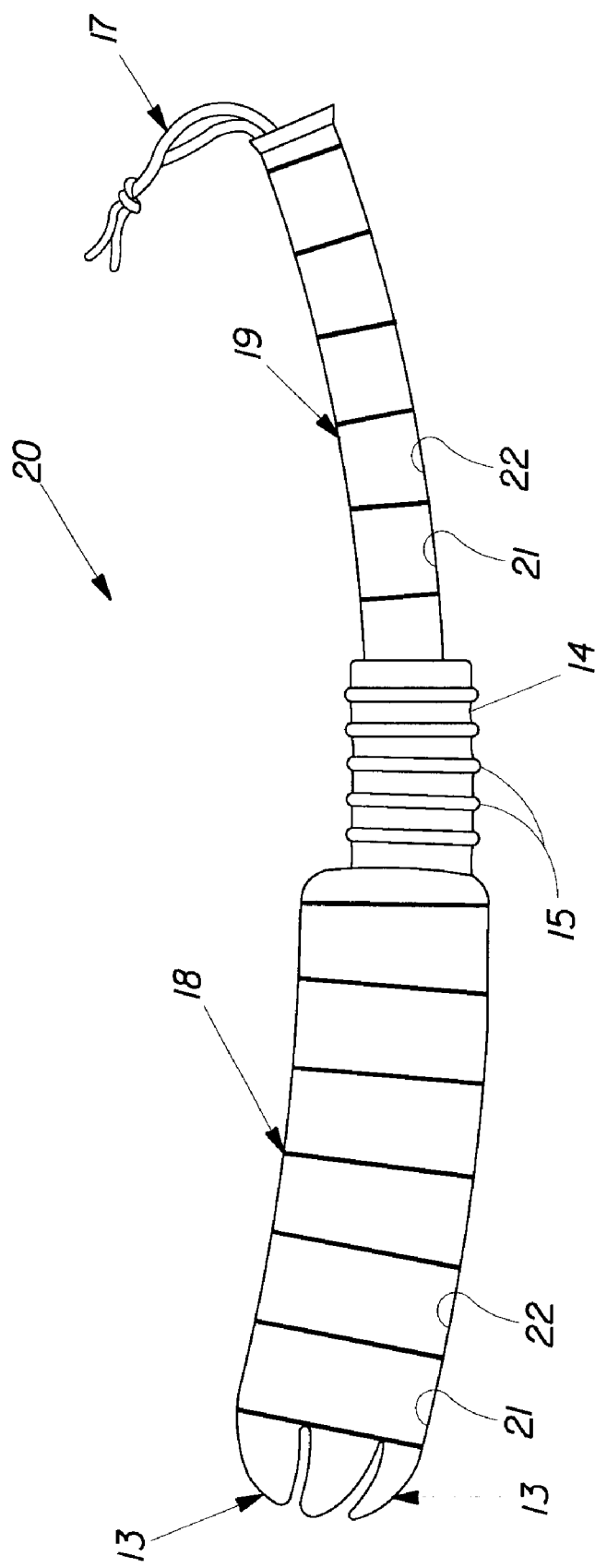

The inner tubular member or plunger as referred to hereinafter (12) include any known or otherwise effective thermoplastic plunger designed to be slidable and telescopically mounted within the finger grip ring (14) such that the plunger (12) can urge the pledget through the flexible petal tips (13) for insertion of the pledget into a woman's vagina.

FIG. 2 is a cross-sectional view of a flushable tampon applicator of the present invention depicting a pledget absorbent device (16) positioned in the thermoplastic, cylindricallly shaped outer tubular member (11). A withdrawal string (17) is permanently attached to one end of the pledget (16) and provides a means of withdrawing the soiled tampon pledget (16) from a woman's vagina.

FIG. 3 is a perspective view of a flushable tampon applicator (20) of the present invention having an outer tubular member (18) and a plunger (19), both of which are constructed from a composite of thermoplastic materials. The composite structure includes one or more units of water-dispersible thermoplastic polymers (21) affixed to one or more units of biodegradable polymers (22) such that the units are arranged in an alternating striped configuration. The composite structure can also be constructed such that the alternating units of water-dispersible and biodegradable polymers are arranged in a concentric ring configuration or a layered structure of composite materials.

It should be noted that although the outer tubular members (11) and (18) are shown as having cylindrical shapes, the outer tubular members(11) and (18) can also be of square, elliptical, conical, or oval configurations. Likewise, the plungers (12) and (19), which are typically of an oval configuration, can be configured in other shapes such as square, hemispherical, conical, and elliptical. The outer tubular members and plungers described herein can be constructed from clear, translucent, transparent, colored, or opaque thermoplastic materials, or combinations thereof.

DETAILED DESCRIPTION OF THE INVENTION

The flushable tampon applicators of the present invention comprise an outer tubular member and plunger made from water-dispersible and biodegradable materials that provide for tampon applicators that are readily disposed by flushing the applicator down a toilet, by biodegradable means, and/or by waste disposal means at a municipal waste treatment facility.

The term "flushable" as used herein refers to materials which are capable of dissolving, dispersing, disintegrating, and/or decomposing in a septic tank such as a toilet to provide clearance when flushed down the toilet without clogging the toilet or any other sewage drainage pipe.

The term "water-dispersible" as used herein refers to materials that readily break apart in unrecognizable pieces upon contact with water as a result of dissolution, solubilization, dissipation, agitation, softening, or any other chemical or mechanical dispersion means.

The term "biodegradable" as used herein refers to materials that when disposed of after use will physically and biologically decompose using known degradation procedures including aerobic, anaerobic, and microbial digestion processes. The biodegradable materials described herein include those degradable water-insoluble materials that will also physically and biologically decompose after disposal in a sewage system.

The term "ambient conditions" as used herein refers to surrounding conditions at about one atmosphere of pressure, at about 50% relative humidity, at about 25° C.

The water-dispersible and biodegradable thermoplastic polymers described herein can be generally defined according to their weight or number average molecular weight. The weight average molecular weight ($M_w$) of a polymer is the summation of the number of polymer molecules and the squared sum of individual polymer molecules molecular weight, divided by the summation of the number of polymer molecules and the sum of individual polymer molecules molecular weight. The number average molecular weight ($M_n$) of a polymer is the weight of a given sample of polymer divided by the number of molecules within the sample. The molecular weight of polymer materials can typically be determined by Size Exclusion Chromatography (SEC) or Gel Permeation Chromatography (GPC) techniques well known in the art.

The thermoplastic polymers described herein are used to construct the outer tubular member and plunger components of the flushable tampon applicators of the present invention. These outer tubular member and plunger components each have a density of from about 1.0 grams per cubic centimeter (g/cm$^3$) to about 1.5 g/cm$^3$. Thermoplastic components having a density of about 1.0 g/cm$^3$ or greater will easily fall to the bottom of a septic tank such as a toilet, resulting in disposal of the thermoplastic components without the need of repeated flushings. The density of a given thermoplastic material and/or components made from the material, will be dependent upon the molecular weight of that material and/or its final product form. Therefore, if an individual thermoplastic material does not have a density of at least about 1.0 g/cm$^3$, the thermoplastic material can be combined with other thermoplastic materials and/or optional ingredients described herein to make suitable outer tubular members and plungers having a density of at least about 1.0 g/cm³. Density values of the outer tubular and plunger components herein can be determined by any known or otherwise effective method for determining the density of thermoplastic materials and final products made from these materials.

The flushable tampon applicators of the present invention can comprise, consist of, or consist essentially of the elements and limitations of the invention described herein, as well as any of the additional or optional ingredients, components, or limitations described herein.

All percentages, parts and ratios are by weight of the total applicator device, unless otherwise specified. All such weights as they pertain to listed ingredients are based on the specific ingredient level and, therefore, do not include carriers or by-products that may be included in commercially available materials, unless otherwise specified.

Applicator Components

The flushable tampon applicators of the present invention typically comprise an outer tubular member and a plunger made from any known or otherwise effective thermoplastic materials that can readily disintegrate upon contact with water such as toilet water. The thermoplastic materials are preferably combinations of water-dispersible and biodegradable polymers that are structurally stable before and during use while also being capable of rapid disintegration in a toilet sewage system to provide disposal via the toilet to further enhance any additional disposal such as further disposal treatment of biodegradation and/or municipal waste disposal.

The outer tubular member and plunger components of the flushable tampon applicator of the present invention can be constructed from the same or otherwise different water-dispersible and biodegradable materials. In other words, the outer tubular member and plunger both can be made from an individual or combination of water-dispersible materials; the outer tubular member and plunger both can be made for an individual or combination of biodegradable materials; the outer tubular member and plunger both can be made from a combination of water-dispersible and biodegradable materials; the outer tubular member can be made from water-dispersible materials and the plunger can be made from biodegradable materials; or the outer tubular member can be made from biodegradable materials and the plunger can be made from water-dispersible materials. The water-dispersible and biodegradable materials from which the outer tubular member and plunger can be made are described in detail hereinbelow.

Water-Dispersible Components

The flushable tampon applicators of the present invention comprise a total of from about 1% to about 99%, preferably from about 10% to about 90%, more preferably from about 20% to about 80% of water-dispersible thermoplastic polymers by weight of the applicator. The water-dispersible thermoplastic polymers can be used individually or as a combination of polymers provided that the water-dispersible thermoplastic polymers can readily disintegrate in water, and can be combined with one or more biodegradable polymers described hereinafter.

The water-dispersible thermoplastic polymers suitable for use herein include those water-dispersible compounds that can readily disintegrate in water such as toilet water while being structurally stable before contact with the water. The terms "structurally stable" and "structural stability" are used interchangeably herein to refer to materials that maintain their molded shape, form, and chemical composition before and during use, and that do not become sticky or slimy to the touch upon contact with moisture-laden air and/or moist human tissue.

Nonlimiting examples of suitable water-dispersible thermoplastic polymers include high molecular weight polyethylene oxides, low molecular weight polyethylene glycols, polyethylene/polypropylene oxide copolymers, polyethylene/polybutylene oxide copolymers polyethylene/polypropylene glycol copolymers, thermoplastic starch polymers, polyvinyl alcohols, partially hydrolyzed polyvinyl alcohols, modified polyvinyl alcohols, infrared treated polyvinyl alcohols, cross-linked polyvinyl alcohols such as a polyvinyl alcohol cross-linked with an aldehyde, alkali metal sulfonate thermoplastic polyesters, hydroxyethyl celluloses, hydroxypropyl celluloses, methylated hydroxypropyl celluloses, polyacrylic acids, polyaspartic acids, polymethacrylic acids, polysaccharides excluding sucrose polysaccharides suitable for use as a plasticizing agent herein, proteins, polyvinyl pyrrolidone homopolymers, polyvinyl pyrrolidone copolymers including polyvinyl pyrrolidone/vinyl acetate copolymers and polyvinyl pyrrolidone/acrylic acid copolymers, polyvinyl methyl ether homopolymers, polyoxazolines including polyethyloxazoline and poly(2-isopropyl-2-oxazoline), polyvinyl methyl oxazolidones, polyvinyl methyl oxazolidimones, polyethylenimines, polyacrylamides, polyvinyl methyl ether/maleic anhydride copolymers, water-dispersible polyurethanes, water-dispersible sulfonate polyesters, and mixtures thereof. Preferred water-dispersible thermoplastic polymers include high molecular weight polyethylene oxides and low molecular weight polyethylene glycols.

Preferred high molecular weight polyethylene oxides and low molecular weight polyethylene glycols suitable for use as water-dispersible thermoplastic polymers herein include those polyethylene oxides and polyethylene glycols which conform to the formula:

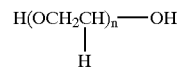

and those polyethylene glycols which conform to the formula:

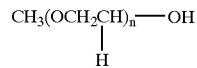

wherein n has an average value of from about 500 to about 180,000, preferably from about 650 to about 50,000, more preferably from about 800 to about 25,000, for high molecular weight polyethylene oxides; and an average value of from about 12 to about 465, preferably from about 12 to about 341, more preferably from about 13 to about 227, for low molecular weight polyethylene glycols. These materials are polymers of ethylene oxide, which are also known as polyethylene oxides, polyoxyethylenes, polyethylene glycols, and polymethoxyethylene glycols.

Specific examples of preferred high molecular weight polyethylene oxides suitable for use as a water-dispersible thermoplastic polymer herein include, but are not limited to, polyethylene oxides having repeating alkylene oxide radicals in the ranges described hereinabove, and a weight average molecular weight of from about 65,000 daltons to about 8,000,000 daltons, preferably from about 80,000 daltons to about 2,000,000 daltons, more preferably from about 100,000 daltons to about 900,000 daltons. These polyethylene oxide polymers are prepared by methods known in the art for making high molecular weight copolymers and interpolymers of ethylene oxide. For example, the high molecular weight copolymers of polyethylene oxide are prepared using ionic catalysts to react ethylene oxide with oxirane compounds such as styrene oxide, propylene oxide, butylene oxide, and the like. High molecular weight interpolymers of polyethylene oxide are prepared by co-polymerizing polyethylene oxide with one or more vinyl monomers such as N,N-dimethylaminoethyl methacrylate, styrene, methyl methacrylate, 2-methyl-5-vinyl pyridine, acrylonitrile, hydroxyethyl methacrylate, acrylic acid, acrylamide, and the like. Grafted or chemically modified high molecular weight polyethylene oxides are also suitable for use as a water-dispersible thermoplastic polymer herein.

The weight average molecular weight ($M^w$) of the high molecular weight polyethylene oxides can be determined by measuring the intrinsic viscosity of a polyethylene oxide material in water at 30° C. The intrinsic viscosity, $[\eta]$, is correlated to the $M_w$ of polyethylene oxide materials, and can be expressed by the following equation: $[\eta]=1.25\times10^{-4}M_w^{0.78}$.

Examples of commercially available high molecular weight polyethylene oxide polymers are the polyethylene oxides which are sold under the tradename POLYOX®, and which are available from the Union Carbide Corporation located in Danbury, Conn. Specific examples of such polyethylene oxides include POLYOX® WSR-10 which has a $M_w$ of about 100,000; POLYOX® WSR-80 which has a $M_w$ of about 200,000; POLYOX® WSR-N-750 which has a $M_w$ of about 300,000; POLYOX® WSR-N-3000 which has a $M_w$ of about 400,000; POLYOX® WSR-3333 which has a $M_w$ of about 400,000; POLYOX® WSR-205 which has a $M_w$ of about 600,000; POLYOX® WSR-1105 which has a $M_w$ of about 900,000; POLYOX® WSR-N-K12 which has a $M_w$ of about 1,000,000; POLYOX® WSR-N-K60 which has a $M_w$ of about 2,000,000; POLYOX® WSR-301 which has a $M_w$ of about 4,000,000; POLYOX® WSR Coagulant which has a $M_w$ of about 5,000,000; POLYOX® WSR-303 which has a $M_w$ of about 7,000,000; POLYOX® WSR-308 which has a $M_w$ of about 8,000,000; and mixtures thereof.

Specific examples of preferred low molecular weight polyethylene glycols suitable for use as a water-dispersible thermoplastic polymer herein include, but are not limited to, polyethylene glycols having repeating alkylene oxide radicals in the ranges described hereinabove, and a number average molecular weight of from about 500 daltons to about 20,000 daltons, preferably from about 550 daltons to about 15,000 daltons, more preferably from about 600 daltons to about 10,000 daltons. The number average molecular weight ($M_n$) of the low molecular weight polyethylene glycols can be determined by known titration procedures used to determine the number of molecules having hydroxy-end groups wherein the $M_n$ is calculated based on the weight of a given polyethylene glycol divided by the number of hydroxy-end group-containing molecules within the polyethylene glycol polymer.

Nonlimiting examples of the preferred low molecular weight polyethylene glycols include those polyethylene glycols (PEG) and polymethoxyethylene glycols MPEG) that are commercially available from Union Carbide, and sold as PEG-600 which has a $M_n$ of about 600; PEG-900 which has a $M_n$ of about 900; PEG-1000 which has a $M_n$ of about 1000; PEG-1450 which has a $M_n$ of about 1450; PEG-335 which has a $M_n$ of about 3350; PEG-4000 which has a $M_n$ of about 4,000; PEG-4600 which has a $M_n$ of about 4600; PEG-8000 which has a $M_n$ of about 8,000; MPEG-550 which has a $M_n$ of about 550; MPEG-750 which has a $M_n$ of about 750; MPEG-2000 which has a $M_n$ of about 2,000; MPEG-5000 which has a $M_n$ of about 5,000; and mixtures thereof.

Specific examples of polyvinyl alcohols suitable for use as a water-dispersible thermoplastic polymer herein include, but are not limited to, those water-soluble thermoplastic polymers prepared by the partial or complete hydrolysis of polyvinyl acetate. The degree of hydrolysis of polyvinyl acetate results in polyvinyl alcohols having different residual acetyl groups and therefore different molecular weight and viscosity characteristics. Accordingly, the water solubility of the polyvinyl alcohol can be regulated by controlling the hydrolysis, molecular weight, and viscosity of the specific polyvinyl alcohol resin. Nonlimiting examples of such suitable polyvinyl alcohols include polyvinyl alcohols having a percent hydrolysis of from about 74% to about 98%, specific nonlimiting examples of which include polyvinyl alcohol 98% hydrolyzed ultra low viscosity resin having a viscosity of from about 3.2 centipoises (cps) to about 4.2 cps, and a weight average molecular weight of from about 13,000 daltons to about 23,000 daltons; polyvinyl alcohol 88% hydrolyzed ultra low viscosity resin having a viscosity of from about 3.0 cps to about 4.0 cps, and a weight average molecular weight of from about 13,000 daltons to about 23,000 daltons; polyvinyl alcohol 88% hydrolyzed low viscosity resin having a viscosity of from about 5.2 cps to about 6.2 cps, and a weight average molecular weight of from about 31,000 daltons to about 50,000 daltons; and mixtures thereof.

The viscosity of the polvinyl alcohols and any other suitable thermoplastic polymer and optional ingredient described herein are measured or determined under ambient conditions, unless otherwise specified, using suitable methods known in the art. Examples of methods for measuring or determining viscosity include method DIN 53 015 which involves the use of a Hoppler falling-ball viscometer for measuring dynamic viscosity in units of Pascal-seconds (Pa-s), and methods DIN 53 562 and DIN 53 012 which involve the use of a Ubbelohde glass capillary viscometer to measure kinematic viscosity in units of square centimeters per second ($cm^2$/sec).

Other examples of suitable polyvinyl alcohols include, but are not limited to, water dispersible polyvinly alcohol resins that have been modified to contain pendant alcohol groups. These modified poylvinyl alcohols can be produced by polymerizing a polyethylene oxide acrylate with vinyl acetate and then hydrolyzing the resultant polymer to produce pendant alcohol groups. Modified polyvinyl alcohols prepared by this procedure typically have viscosities ranging from about 500 poise to about 4,500 poise dependent upon the shear rate used to form the modified polyvinyl alcohol into a molded thermoplastic polymer. Examples of commercially available modified polyvinyl alcohols include those modified polyvinyl alcohol resins manufactured by Texas Polymer Services Incorporated (Houston, Tex.), and sold under the VINEX and AIRVOL tradenames. Specific examples of commercially available VINEX resins include, but are not limited to, VINEX 2019, VINEX 2025, VINEX 2034, and VINEX 2144. Specific examples of AIRVOL resins include, but are not limited to, AIRVOL 125 and AIRVOL 325.

Other examples of suitable polyvinyl alcohols include, but are not limited to, the polyvinyl alcohols that are commercially available from Clariant GmbH (Sulzbach, Germany) under the MOWIOL tradename. Specific examples of MOWIOL resins include MOWIOL 18–88, MOWIOL 26–88, and MOWIOL 30–92.

Nonlimiting specific examples of alkali metal sulfonate polyesters suitable for use as a water-dispersible thermoplastic polymer herein include those water-dispersible, linear thermoplastic polyesters which contain carbonyloxy-linking groups in the linear, molecular structure. The alkali metal sulfonate polyesters are typically prepared by reacting at least one difunctional dicarboxylic acid, at least one diol, and at least one difunctional sulfomonomer containing at least one metal sulfonate group attached to an aromatic nucleus having the functional group carboxyl. The number average molecular weight of suitable alkali metal sulfonate polyesters ranges from about 13,000 daltons to about 19,000 daltons, based on the number of repeating sulfomonomer groups in the molecule. It is believed that the sulfomonomer substituent is primarily responsible for the water dispersibility of the thermoplastic polyester. Nonlimiting examples of commercially available water-dispersible, linear thermoplastic polyesters include the alkali metal sulfonates sold under the tradename Eastman AQ® polymer from Eastman Chemical Products, Incorporation located in Kingsport, Tenn., specific examples of which include Eastman AQ® 1045, Eastman AQ® 1350, Eastman AQ® 1950, Eastman AQ® 14,000, Eastman AQ® 29S, Eastman LB-100 AQ® 29S, Eastman AQ® 55S, Eastman AQ® 38S, Eastman AQ® 48, and mixtures thereof.

Biodegradable Components

The flushable tampon applicators of the present invention comprise a total of from about 1% to about 99%, preferably from about 9% to about 59%, more preferably from about 15% to about 50% of biodegradable thermoplastic polymers by weight of the applicator. The biodegradable thermoplastic polymers can be used individually or as a combination of polymers provided that the biodegradable thermoplastic polymers are degradable by biological and environmental means, and that they are compatible for combination with one or more water-dispersible polymers described hereinabove.

The biodegradable polymers suitable for use herein are those biodegradable materials which are susceptible to being assimilated by microorganisms such as molds, fungi, and bacteria when the biodegradable material is buried in the ground or otherwise comes in contact with the microorganisms including contact under environmental conditions conducive to the growth of the microorganisms. Suitable biodegradable polymers also include those biodegradable materials which are environmentally degradable using aerobic or anerobic digestion procedures, or by virtue of being exposed to environmental elements such as sunlight, rain, moisture, wind, temperature, and the like.

Nonlimiting examples of biodegradable thermoplastic polymers suitable for use in the flushable tampon applicators of the present invention include aliphatic polyesteramides; diacids/diols aliphatic polyesters; aromatic polyesters including polyethylene terephthalates (PETs), modified polyethylene terephthalates, polybutylene terephthalates (PBTs); aliphatic/aromatic copolyesters; polycaprolactones; poly(3-hydroxyalkanoates) including poly(3-hydroxybutyrates), poly(3-hydroxyhexanoates), and poly(3-hydroxyvalerates); poly(3-hydroxyalkanoates) copolymers including poly(3-hydroxy) butyrate/valerate copolymers; polyesters and polyurethanes derived from aliphatic polyols (i.e., dialkanoyl polymers); polyamides including Nylon 6, Nylon 11, Nylon 12, Nylon 46, and Nylon 66; polyvinyl acetates; polyethylene/vinyl acetate copolymers; polyethylene/vinyl alcohol copolymers; polyethylene/methacrylic acid copolymers; polystyrene/methyl methacrylate copolymers; polymethyl methacrylates; low density polyethylenes; linear low density polyethylenes; ultra low density polyethylenes; high density polyethylenes; lactic acid polymers including lactic acid homopolymers and lactic acid copolymers; lactide polymers including lactide homopolymers and lactide copolymers; glycolide polymers including glycolide homopolymers and glycolide copolymers; and mixtures thereof. Preferred are aliphatic polyesteramides, diacids/diols aliphatic polyesters, aliphatic/aromatic copolyesters, lactic acid polymers, and lactide polymers. Aliphatic polyesteramides are most preferred.

Specific examples of preferred aliphatic polyesteramides suitable for use as a biodegradable thermoplastic polymer herein include, but are not limited to, aliphatic polyesteramides which are reaction products of a synthesis reaction of diols, dicarboxylic acids, and aminocarboxylic acids; aliphatic polyesteramides formed from reacting lactic acid with diamines and dicarboxylic acid dichlorides; aliphatic polyesteramides formed from caprolactone and caprolactam; aliphatic polyesteramides formed by reacting acid-terminated aliphatic ester prepolymers with aromatic diisocyanates; aliphatic polyesteramides formed by reacting aliphatic esters with aliphatic amides; and mixtures thereof. Aliphatic polyesteramides formed by reacting aliphatic esters with aliphatic amides are most preferred.

Preferred aliphatic polyesteramides which are copolymers of aliphatic esters and aliphatic amides can be characterized in that these copolymers generally contain from about 30% to about 70%, preferably from about 40% to about 80% by weight of aliphatic esters, and from about 70% to about 30%, preferably from about 60% to about 20% by weight of aliphatic amides. The weight average molecular weight of these copolymers ranges from about 10,000 daltons to about 500,000 daltons, preferably from about 20,000 daltons to about 300,000 daltons as measured by known gel chromatography techniques used in the determination of molecular weight of polymers.

The aliphatic ester and aliphatic amide copolymers of the preferred aliphatic polyesteramides are derived from monomers such as dialcohols including ethylene glycol, diethylene glycol, 1,4-butanediol, 1,3-propanediol, 1,6-hexanediol, and the like; dicarboxylic acids and dicarboxylic acid esters including oxalic acid, succinic acid, adipic acid, oxalic acid esters, succinic acid esters, adipic acid esters, and the like; hydroxycarboxylic acid and lactones including caprolactone, and the like; aminoalcohols including ethanolamine, propanolamine, and the like; cyclic lactams including ε-caprolactam, lauric lactam, and the like; ω-aminocarboxylic acids including aminocaproic acid, and the like; 1:1 salts of dicarboxylic acids and diamines including 1:1 salt mixtures of dicarboxylic acids such as adipic acid, succinic acid, and the like, and diamines such as hexamethylenediamine, diaminobutane, and the like; and mixtures thereof. Hydroxy-terminated or acid-terminated polyesters such as acid terminated oligoesters can also be used as the ester-forming compound. The hydroxy-terminated or acid terminated polyesters typically have number average molecular weights of from about 200 daltons to about 10,000 daltons.

The preferred aliphatic polyesteramides can be prepared by any suitable synthesis or stoichiometric technique known in the art for forming aliphatic polyesteramides having aliphatic ester and aliphatic amide monomers. A typical synthesis involves stoichiometrically mixing the starting monomers, optionally adding water to the reaction mixture, polymerizing the monomers at an elevated temperature of about 220° C., and subsequently removing the water and excess monomers by distillation using vacuum and elevated temperature, resulting in a final copolymer of an aliphatic polyesteramide. Other suitable techniques involve transesterification and transamidation reaction procedures. As apparent by those skilled in the art, a catalyst can be used in the above-described synthesis reaction and transesterification or transamidation procedures, wherein suitable catalysts include phosphorous compounds, acid catalysts, magnesium acetates, zinc acetates, calcium acetates, lysine, lysine derivatives, and the like.

The preferred aliphatic polyesteramides comprise copolymer combinations of adipic acid, 1,4-butanediol, and 6-aminocaproic acid with an ester portion of 45%; adipic acid, 1,4-butanediol, and ε-caprolactam with an ester portion of 50%; adipic acid, 1,4-butanediol, and a 1:1 salt of adipic acid ("AH salt") and 1,6-hexamethylenediamine; and an acid-terminated oligoester made from adipic acid, 1,4-butanediol, 1,6-hexamethylenediamine, and ε-caprolactam. These preferred aliphatic polyesteramides have melting points of from about 115° C. to about 155° C. and relative viscosities (1 wt. % in m-cresol at 25° C.) of from about 2.0 to about 3.0, and are commercially available from Bayer Aktiengesellschaft located in Leverkusen, Germany under the BAK® tradename. Specific examples of such commercially available polyesteramides include BAK® 402, BAK® 403, and BAK® 404.

Specific examples of preferred diacids/diols aliphatic polyesters suitable for use as a biodegradable thermoplastic polymer herein include, but are not limited to, aliphatic polyesters produced either from ring opening reactions or from the condensation polymerization of acids and alcohols, wherein the number average molecular weight of these aliphatic polyesters typically range from about 30,000 daltons to about 300,000 daltons. The preferred diacids/diols aliphatic polyesters are reaction products of a $C_2$–$C_{10}$ diol reacted with oxalic acid, succinic acid, adipic acid, suberic acid, sebacic acid, copolymers thereof, or mixtures thereof. Nonlimting examples of preferred diacids/diols aliphatic polyesters include polyalkylene succinates such as polyethylene succinate, and polybutylene succinate; polyalkylene succinate copolymers such as polyethylene succinate/adipate copolymer, and polybutylene succinate/adipate copolymer; polypentamethyl succinates; polyhexamethyl succinates; polyheptamethyl succinates; polyoctamethyl succinates; polyalkylene oxalates such as polyethylene oxalate, and polybutylene oxalate; polyalkylene oxalate copolymers such as polybutylene oxalate/succinate copolymer and polybutylene oxalate/adipate copolymer; polybutylene oxalate/succinate/adipate terpolymers; and mixtures thereof. An example of suitable commercial diacid/diol aliphatic polyesters is the polybutylene succinate/adipate copolymers sold under the BIONOLLE 1000 and BIONOLLE 3000 tradenames from the Showa Highpolymer Company, Ltd. located in Tokyo, Japan.

Specific examples of preferred aliphatic/aromatic copolyesters suitable for use as a biodegradable thermoplastic polymer herein include, but are not limited to, those aliphatic/aromatic copolyesters that are random copolymers formed from a condensation reaction of dicarboxylic acids or derivatives thereof and diols. Suitable dicarboxylic acids include, but are not limited to, malonic, succinic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, 2,5-norbornanedicarboxylic, 1,4-terephthalic, 1,3-terephthalic, 2,6-naphthoic, 1,5-naphthoic, ester forming derivatives thereof, and combinations thereof. Suitable diols include, but are not limited to, ethylene glycol, diethylene glycol, triethylene glycol, tetraethylene glycol, propylene glycol, 1,3-propanediol, 2,2-dimethyl-1,3-propanediol, 1,3-butanediol, 1,4-butanediol, 1,5-pentanediol, 1,6-hexanediol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, and combinations thereof. Nonlimiting examples of such aliphatic/aromatic copolyesters include a 50/50 blend of poly(tetramethylene glutarate-co-terephthalate), a 60/40 blend of poly(tetramethylene glutarate-co-terephthalate), a 70/30 blend of poly(tetramethylene glutarate-co-terephthalate), an 85/15 blend of poly(tetramethylene glutarate-co-terephthalate), a 50/45/5 blend of poly(tetramethylene glutarate-co-terephthalate-co-diglycolate), a 70/30 blend of poly(ethylene glutarate-co-terephthalate), an 85/15 blend of poly(tetramethylene adipate-co-terephthalate), an 85/15 blend of poly(tetramethylene succinate-co-terephthalate), a 50/50 blend of poly(tetramethylene-co-ethylene glutarate-co-terephthalate), and a 70/30 blend of poly(tetramethylene-co-ethylene glutarate-co-terephthalate). These aliphatic/aromatic copolyesters, in addition to other suitable aliphatic/aromatic polyesters, are further described in U.S. Pat. No. 5,292,783 issued to Buchanan et al. on Mar. 8, 1994, which descriptions are incorporated by reference herein. The poly(tetramethylene adipate-co-terephthalate) is a preferred aliphatic/aromatic copolyester that is commercially available from Eastman Chemical (Kingsport, Tenn.) under the Eastar Biodegradable Copolyester 14776 tradename.

Specific examples of preferred lactic acid polymers and lactide polymers suitable for use as a biodegradable thermoplastic polymer herein include, but are not limited to, those polylactic acid-based polymers and polylactide-based polymers that are generally referred to in the industry as "PLA". Therefore, the terms "polylactic acid", "polylactide" and "PLA" are used interchangeably to include homopolymers and copolymers of lactic acid and lactide based on polymer characterization of the polymers being formed from a specific monomer or the polymers being comprised of the smallest repeating monomer units. In other words, polylatide is a dimeric ester of lactic acid and can be formed to contain small repeating monomer units of lactic acid (actually residues of lactic acid) or be manufactured by polymerization of a lactide monomer, resulting in polylatide being referred to both as a lactic acid residue containing polymer and as a lactide residue containing polymer. It should be understood, however, that the terms "polylactic acid", "polylactide", and "PLA" are not intended to be limiting with respect to the manner in which the polymer is formed.

The polylactic acid polymers generally have a lactic acid residue repeating monomer unit that conforms to the following formula:

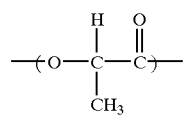

The polylactide polymers generally having lactic acid residue repeating monomer units as described herein-above, or lactide residue repeating monomer units that conform to the following formula:

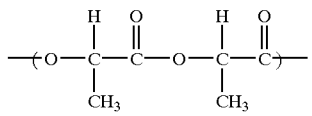

Typically, polymerization of lactic acid and lactide will result in polymers comprising at least about 50% by weight of lactic acid residue repeating units, lactide residue repeating units, or combinations thereof. These lactic acid and lactide polymers include homopolymers and copolymers such as random and/or block copolymers of lactic acid and/or lactide. The lactic acid residue repeating monomer units can be obtained from L-lactic acid and D-lactic acid. The lactide residue repeating monomer units can be obtained from L-lactide, D-lactide, and meso-lactide.

Suitable lactic acid and lactide polymers include those homopolymers and copolymers of lactic acid and/or lactide which have a weight average molecular weight generally ranging from about 10,000 daltons to about 600,000 daltons. An example of commercially available polylactic acid polymers includes a variety of polylactic acids that are available from the Chronopol Incorporation located in Golden, Colo. An example of commercially available polylactide polymers includes the polylactides sold under the tradename Eco-PLA®. An example of commercially available "PLA" polymers includes PLA 44D and PLA 62–50, both of which are available from Cargill-Dow Polymers, LLC located in Minnetonka, Minn. Other suitable polylactic acid polymers and copolymers include polylactic acid prepared by direct polycondensation of lactic acid (available from the Mitsui Chemical Incorporation under the tradename LACEA), and a block copolymer comprising a polylactic acid hard segment and a polyoxyalkylene dialkanoate soft segment (available from the Dainippon Ink and Chemicals Incorporation and the Shimadzu Corporation, both of which are located in Japan).

Specific examples of other suitable biodegradable polymers include polycaprolactone polyesters having a number average molecular weight of from about 10,000 daltons to about 80,000 daltons. Commercially suitable polycaprolactone polymers are the polycaprolactones available from the Union Carbide Corporation sold under the TONE tradename, examples of which include Tone P-767, Tone P-787, and Tone P-303. Tone P-767 has a number average molecular weight of about 43,000 daltons. Tone P-787 has a number average molecular weight of about 80,000 daltons. Tone P-303 is an A-B-A block polymer of Tone P-767 polycaprolactone and polyethylene oxide, and has a number average molecular weight of from about 30,000 daltons to about 35,000 daltons.

The biodegradable polymers described herein, in addition to thermoplastic compositions containing these polymers, will physically and biologically decompose using known degradation procedures such as aerobic, anaerobic, and microbial digestion processes. One such method of evaluating the decomposition of biodegradable materials includes an anaerobic disintegration procedure which involves measuring the percent weight loss of thermoplastic compositions containing biodegradable polymers. Typically, thermoplastic compositions containing biodegradable polymers are exposed to anaerobic sludge that can be obtained from a municipal wastewater treatment plant (e.g., sludge that has a pH of or between about 7 and 8, and about 1% total solids). The sludge-exposed thermoplastic compositions are allowed to disintegrate or decompose for 7, 14, and 28 days at 35° C. under controlled incubator conditions. After the 7, 14, or 28 day incubation period, the sludge-exposed thermoplastic compositions are evaluated for percent weight loss by recovering any undisintegrated portions of the compositions, drying these undisintegrtaed portions at 40° C. for at least 2 hours after a tap water rinsing, and determining the weight of the dried undisintegrated portions. The percent weight loss is calculated based on the weight of the thermoplastic compositions before and after exposure to sludge for a given time period. It has been found that the biodegradable polymer containing-thermoplastic compositions described herein lose their structural integrity by breaking apart into smaller pieces and/or by shrinking into smaller fragments after being exposed to sludge for only 7 days. Anaerobic biodegradation of these biodegradable polymer containing-thermoplastic compositions increased after the compositions were exposed to sludge for periods of 14 and 28 days.

Preferred Embodiments

The flushable tampon applicators of the present invention preferably comprise a blend of water-dispersible and biodegradable materials, wherein this blend can be defined as a combination of one or more high molecular weight polyethylene oxides, one or more low molecular weight polyethylene glycols, and one or more aliphatic polyesteramides. In this context, the term "blend" refers to a composition of thermoplastic materials that has been formed by melt processing two or more thermoplastic materials to result in a homogenous, heterogeneous, or mixture thereof, of these materials. It has been found that a thermoplastic blend comprising a combination of high molecular weight polyethylene oxides, low molecular weight polyethylene glycols, and aliphatic polyestermides provides a flushable tampon applicator that readily disintegrates in water, that has improved aesthetics such as non-sticky, non-slimy, air-laden moisture resistance, softness, flexibility, and that is of little or no environmental concern for disposal.

The combination of the high molecular weight polyethylene oxides, low molecular weight polyethylene glycols, and aliphatic polyestermides results in a thermoplastic composition comprising a total of from about 1% to about 90% by weight of high molecular weight polyethylene oxides, a total of from about 1% to about 40% by weight of low molecular weight polyethylene glycols, and a total of from about 9% to about 59% by weight of aliphatic polyesteramides. Therefore, the thermoplastic compositions can comprise blended ratios of water-dispersible materials such as high molecular weight polyethylene oxides and low molecular weight polyethylene glycols to biodegradable materials such as aliphatic polyesteramides of from about 10:1 to about 1:6, preferably of from about 4:1 to about 1:1. The ratio of water-dispersible materials, such as a ratio of high molecular weight polyethylene oxide to low molecular weight polyethylene glycol, typically ranges from about 9:1 to about 1:4, preferably from about 3:1 to about 1:2.

The flushable tampon applicators of the present invention can also comprise other blends of water-dispersible and biodegradable thermoplastic polymers, nonlimiting examples of which include a blend of one or more high molecular weight polyethylene oxides, one or more low molecular weight polyethylene glycols, and one or more aliphatic polyesters; a blend of one or more high molecular weight polyethylene oxides, one or more low molecular weight polyethylene glycols, and one or more aliphatic/aromatic polyesters. These blends as well as the above-described preferred thermoplastic polymer blend and any other blend or structure of thermoplastic materials are suitable for forming the outer tubular member and plunger components of the flushable tampon applicators of the present invention.

The flushable tampon applicators of the present invention can also comprise a composite of thermoplastic materials. In this context, the term "composite" refers to a structure of thermoplastic polymeric materials that are intermingled together or joined such that each thermoplastic polymer forms at least one unit of the total composite structure. For example, a thermoplastic composite can contain one or more units of water-dispersible polymers intermixed or joined with one or more units of biodegradable polymers such that within the overall composite structure the water-dispersible polymer units create structural discontinuities between the biodegradable polymer units. In this context, the term "structural discontinuities" refers to discrete or separate components that are joined or intermingled to provide adjacent or alternate units of individual components. Preferably, a thermoplastic composite is constructed such that it comprises less than about 70% of water-dispersible polymers and more than about 30% of biodegradable polymers, more preferably less than about 50% of water-dispersible polymers and more than about 50% of biodegradable polymers, even more preferably less than about 30% of water-dispersible polymers and more than about 70% of biodegradable polymers, by weight of the composite. However, the thermoplastic composites can be any composite combination of water-dispersible and biodegradable polymers described herein provided that the water-dispersible polymers allow for rapid dispersion of the biodegradable polymers into separate components so that the overall composite structure readily disintegrates upon contact with water. The thermoplastic composite tampon applicators can be constructed using known procedures such as injection molding and co-injection molding which eliminate the need to assemble separate composite pieces for producing a final tampon applicator product. Alternatively, the thermoplastic composite tampon applicators can be constructed by molding separate composite pieces and assembling or joining the pieces into a final tampon applicator product, wherein means of assembling or joining the composite pieces include adhesive bonding, heat sealing, ultrasonic welding, solvent welding, dielectric sealing, and mechanical attachment. The flushable tampon applicators of the present invention made from thermoplastic composites have been found to be readily disposed of by flushing down a sewage system such as a toilet and by the disclosed biodegradation procedures. The composite tampon applicators can also be made from a composite structure of thermoplastic polymers combined with paper, cellulose, cellophane, rayon fiber, woven, nonwoven materials, or combinations thereof.

It is contemplated that the flushable tampon applicators of the present invention can be constructed in any other blend, composite, shape, or configuration using the water-dispersible and/or biodegradable thermoplastic polymers described herein. Another nonlimiting preferred embodiment includes spiral shaped flushable tampon applicators made from spirally wound thermoplastic materials that are held together using water-soluble adhesives. The water-soluble adhesive materials may be any known or otherwise effective water-soluble adhesives, but preferably are polyethyloxazoline and methyl cellulose adhesives.

Still yet another nonlimiting embodiment of flushable tampon applicators include composite paper tampon applicators wherein the composite comprises a combination of paper and one or more thermoplastic materials described herein. This combination of paper and thermoplastic polymers can be made into a flushable tampon applicator using various known techniques such as overmolding and insert molding. An example of an overmolding procedure involves placing a paper tube into an injection mold cavity, clamping the mold shut, and injecting a thermoplastic polymer into the cavity such that the paper is encapsulated or partially encapsulated by the thermoplastic material. It is believed that overmolding can provide for a flushable composite paper tampon applicator that resembles flushable plastic tampon applicators since the composite paper tampon applicator contains paper at least partially encapsulated by one or more thermoplastic polymers described herein to result in a composite paper tampon applicator that has a plastic-like feel, look, and/or texture. Composite paper tampon applicators made by insert molding typically results in a tampon applicator product that contains a thin layer of thermoplastic material surrounding a paper tube, an example of such an insert molding procedure involves placing a paper tube along a cavity wall of an injection molding apparatus, clamping the mold shut, injecting a thermoplastic polymer into the mold cavity, and heating the mold under pressure to bond the paper and thermoplastic material. The composite paper tampon applicators described herein can provide not only flushable tampon applicators that have plastic-like features, but that provide a means of minimizing the amount of thermoplastic material needed to form tampon applicator components.

It is preferred that the flushable tampon applicators of the present invention be constructed from thermoplastic materials that are typically in the form of polymer films. It should be understood, however, that these thermoplastic materials are also suitable for use as fibrous materials in the construction of absorbent articles such as tampon pledgets or any other fibrous or nonwoven material.

Composition Morphology

Thermoplastic compositions suitable for use in the manufacture of flushable tampon applicators of the present invention can be a blend or other configuration of polymeric materials which will result in the compositions exhibiting amorphous and crystalline properties that can be characterized in terms of compositional morphology. It has been found that a particular blend of water-dispersible and biodegradable polymers described herein results in a thermoplastic composition having a defined morphology which provides for individual components of the composition to have melt profiles that allows for the creation of crystalline structures in the form of separate regions or domains within the blended mixture of thermoplastic materials. Specifically, it has been found that a thermoplastic composition comprising a blend of high molecular weight polyethylene oxides, low molecular weight polyethylene glycols, and aliphatic polyesteramides or aliphatic/aromatic copolyesters exhibits a morphology such that the polyethylene oxides and polyethylene glycols form a homogenous blend of water-dispersible polymers that surrounds or encloses microdomains of the aliphatic polyesteramides or aliphatic/aromatic polyesters. In this context the term "microdomain" refers to polymer crystalline structures that have particle sizes in the submicron sized region. It has also been found that a thermoplastic composition comprising a blend of water dispersible polymers such as high molecular weight polyethylene oxides and/or low molecular weight polyethylene glycols in combination with biodegradable polymers such as diacids/diols aliphatic polyesters forms a homogeneous one-phase polymer morphology.

The two phase crystalline structure of a continuous phase of water-dispersible polymers and a discontinuous phase of biodegradable polymer microdomains are especially effective in forming thermoplastic compositions that can be melt processed into flushable tampon applicators of the present invention which are readily disposed of without creating any environmental concerns for their disposal. The two-phase crystalline structure has a morphology profile of water-dispersible and biodegradable polymers wherein in the liquid state (temperature above the melting point of the individual polymers), the polymers exhibit a heterogeneous phase morphology, but can be melt processed to result in a solid flushable tampon applicator exhibiting homogenous properties. Therefore, as used herein the term "homogenous" refers to a uniform mixture of materials, whereas the term "heterogeneous" refers to a nonuniform mixture of materials. The phase morphology can be determined using optical and scanning electron microscopes, for example a convenient optical microscopy instrument that can be used to determine the phase morphology of the thermoplastic compositions described herein is the Zeiss Axioplan 2 Mot-Imaging Microscope that is equipped with a Linkham MDS-BCS-600 hot stage and that is available from the Carl Zeiss Incorporation located in Thornwood, N.Y.

The phase morphology of the water-dispersible and biodegradable polymers defined herein can further be described in terms of the polymers glass transition temperatures (Tg). The glass transition temperature of polymers or any other materials is typically identified as the area on the line where a distinct change in slope occurs, and can be determined using a thermal analysis instrument such as the 2980 Dynamic Mechanical Analyzer (DMA) in combination with Thermal Analyst Data Collection software program (Thermal Solutions version 2.5) and Data Analysis software program (Universal Analysis version 2.5H), all of which are available from T. A. Instruments Incorporation of New Castle, Del. It has also been found that combinations of water-dispersible and biodegradable polymers exhibit one or two glass transition temperatures, providing further support of polymers having one- or two-phase morphology profiles. As exemplified in Table 1 hereinbelow, polymer blends of water-dispersible polymers and aliphatic polyesteramides exhibit two different glass transition temperatures indicative of a two-phase morphology wherein polymer blends of water-dispersible polymers and diacids/diols aliphatic polyesters exhibit one glass transition temperature indicative of a one-phase morphology.

It is believed that these morphology properties will also be exhibited in thermoplastic compositions made from a composite or any other configuration of water dispersible and biodegradable polymers described herein.

TABLE 1

Glass Transition Behavior of Water-Dispersible/Biodegradable and Polymer Blends

| Polymers | $Tg_1$ (° C.) | $Tg_2$ (° C.) | $Tg_3$ (° C.) |
|---|---|---|---|
| PEO[1] | −41 | — | — |
| PEO[1]/PEG[2]—40/30 blend | −33 | — | — |
| aliphatic polyesteramide (BAK 404)[3] | — | −7 | — |
| aliphatic-aromatic copolyester (Eastar 14776)[4] | — | −25 | — |
| diacid-diol aliphatic polyester (Bionolle 3001)[5] | — | −31 | — |
| PEO[1]/BAK 404[3]- 75/25 blend | −43 | 8 | — |
| PEO[1]/Eastar 14776[4]- 60/40 blend | −42 | −24 | — |
| PEO[1]/Bionolle 3001[5]- 70/30 blend | — | — | −36 |
| PEO[1]/Bionolle 3001[5]- 50/50 blend | — | — | −28 |
| PEO[1]/Bionolle 3001[5]- 15/85 blend | — | — | −30 |
| PEO[1]/PEG[2]/BAK 404[3]- 40/30/30 blend | −31 | −10 | — |
| PEO[1]/PEG[2]/Eastar 14776[4]- 40/30/30 blend | −41 | −27 | — |
| PEO[1]/PEG[2]/Bionolle 3001[5]- 40/30/30 blend | — | — | −31 |

$Tg_1$- glass transition temperature of water-dispersible polymer(s)
$Tg_2$- glass transition temperature of biodegradable polymer
$Tg_3$- combined glass transition temperature of water-dispersible and biodegradable polymers
[1]polyethylene oxide available as POLYOX ® WSR-80 from the Union Carbide Corporation
[2]polyethylene glycol available as PEG-8000 from Union Carbide
[3]aliphatic polyesteramide available as BAK 404 from Bayer Aktiengesellschaft
[4]aliphatic-aromatic copolyester available as Eastar Biodegradable Copolyester 14776 from Eastman Chemical
[5]diacid-diol aliphatic polyester available as BIONOLLE 3001 from the Showa Highpolymer Company, Ltd.

Physical Properties

The flushable tampon applicators of the present invention are made from thermoplastic compositions having physical properties of tensile strength at break, percent elongation at break, elastic modulus, and hardness.

The tensile strength at break, percent elongation at break, and elastic modulus of thermoplastic materials, especially blends of thermoplastic materials, are determined according to methods known in the art. One such method is the ASTM D882-95a test method described in "Standard Test Method for Tensile Properties of Thin Plastic Sheeting", pages 159–167. This procedure involves testing blends of thermoplastic materials for achieving desired properties of flexibility, elasticity, durability, unbrittleness, resiliency, distensibility, tenacity, and so forth. Typically, blends of thermoplastic materials are injection molded to form "dogbone-shaped" test samples having dimensions of ½ inch length (L)×⅛ inch width (W)×1/16 inch height (H), then the "dogbone-shaped" test samples are evaluated for tensile strength at break, percent elongation at break, and elastic modulus using an Instron Tensile Tester (Model 1122 from Instron Corporation located in Canton, Mass.) equipped with a 50 pound load cell, grip separation of 1 inch, a gage length of ½ inches, 5 millimeter (mm) jaw gap, and a crosshead speed of 2 inches/minute. For each analysis, the "dogbone-shaped" test sample is stretched until breakage occurs, and a load-versus-extension plot is generated for determining the tensile strength at break, percent elongation at break, and elastic modulus properties. The tensile strength at break is the load at break divided by the cross-sectional area of the test sample, and is defined in units of mega-Pascal or MPa (newton/square meter). The percent elongation at break is determined by dividing the length of the extension at the point of rupture by the gage length, and then multiplying by 100. Elastic modulus is the slope of the initial linear portion of the load-extension curve, and is defined in units of MPa.

The thermoplastic compositions described herein preferably have a harness property such that the compositions exhibit a firm resistance to stress or strain, yet are not brittle or too soft for processing into flushable tampon applicators of the present invention. The hardness properties are determined according to ASTM D2240-97 test method described in "Standard Test Method for Rubber Property-Durometer Hardness, pages 388–391. Typically, thermoplastic materials are injected molded into bars that are stacked in groups of two bars per stack wherein each bar stack has a total thickness of ⅛ inches. The hardness value is measured at various points of the bar stack using a hardness instrument such as Model 307 L Shore D Durometer from PTC Instruments, and a mean hardness measurement is determined.

The preferred thermoplastic compositions for constructing the flushable tampon applicators of the present invention have physical properties similar to or superior to physical properties of known thermoplastic materials that are used in the manufacture of tampon applicators. For example, polyethylene-based thermoplastic polymers typically have elastic modulus properties of from about 80 MPa to about 200 MPa, wherein other thermoplastic polymers such as polypropylene-based polymers have elastic modulus of from about 1000 MPa to about 1500 MPa. It has been found that the thermoplastic compositions described herein exhibit desirable properties of an elastic modulus value of less than 1000 MPa, and this elastic modulus attribute in addition to the other described physical properties result in thermoplastic compositions having flexibility, elasticity, durability, resiliency, distensibility, tenacity, and the like. The physical properties of the preferred thermoplastic compositions are exemplified hereinbelow in Table 2.

TABLE 2

Thermoplastic Compositions Physical Properties

| Sample | Tensile Strength at break (MPa) | Percent Elongation at break (%) | Elastic Modulus (MPa) | Hardness (Shore D) |
|---|---|---|---|---|
| PEO[1]/PEG[2]/Biomer 209H[6] (40/30/30 blend) | 6 | 20 | 310 | 58 |
| PEO[1]/PEG[2]/Bionolle 3001[5] (40/30/30 blend) | 8 | 460 | 220 | 51 |
| PEO[1]/PEG[2]/Bionolle 3001[5] (66/17/17 blend) | 5 | 80 | 270 | 52 |
| PEO[1]/PEG[2]/Eastar 14776[4] (40/30/30 blend) | 6 | 80 | 230 | 51 |
| PEO[1]/PEG[2]/BAK 404[3] (40/30/30 blend) | 11 | 20 | 250 | 57 |
| PEO[1]/PEG[2]/BAK 404[3] (40/40/20 blend) | 9 | 20 | 340 | 60 |
| PEO[1]/PEG[2]/BAK[3]/P-645[7] (36/27/27/10 blend) | 8 | 46 | 190 | 51 |
| PEO[1]/PEG[2]/BAK[3]/P-4141[8] (36/27/27/10 blend) | 7 | 48 | 180 | 51 |
| PEO[1]/PEG[2]/PLA 44D[9] (40/30/30 blend) | 19 | 13 | 530 | 67 |
| PEO[1]/PEG[2]/PLA 62-50D[9] (40/30/30 blend) | 22 | 10 | 510 | 67 |

[6]polyhydroxyalkanoate available as Biomer 209H from Biomer, Frost-Kasten-Str., Krailling, Germany
[7]adipate polyester plasticizer available as Plasthall 645 from C. P. Hall
[8]triethylene glycol caprate-caprylate plasticizer available as Plasthall 4141 from C. P. Hall
[9]polylactic acids available as PLA 44D grade and PLA 62-50D grade from Cargill-Dow Polymers, LLC The thermoplastic compositions also have physical properties of dry and wet flexural modulus. The dry flexural modulus is determined according to ASTM D5943-96 test method described in "Standard Test Method for Determining Flexural Properties of Plastics", pages 708–712. This procedure involves injection molding thermoplastic materials into "beams" of test samples having 5 inch L×½ inch W×⅛ inch H. Generally, the test samples are pre-loaded with 0.01 pounds of force, thereafter a force loading is applied at a rate of 0.1 inches per minute, and a stress-versus-strain curve is generated to determine the dry flexural modulus property. The dry flexural modulus is the slope of the stress-strain curve as calculated in the linear region of from about 0.05% to about 0.25% of the flexural strain. The wet flexural modulus is determined by submerging the dry "beams" of test samples in water at time intervals of 5 minutes, 15 minutes, and 60 minutes, and observing the softening of the test samples. As used herein, the term "softening" refers to materials that readily lose their stiffness or undergo a decrease in flexural modulus property upon contact with water. It has been found that the preferred thermoplastic compositions described herein undergo a significant decrease in flexural modulus upon contact of the composition with water. This decrease in flexural modulus property provides for thermoplastic compositions that are manufactured into flushable tampon applicators that readily lose their structural integrity in water for easy disposal down a sewage system such as a toilet. Dry and wet flexural modulus properties of preferred thermoplastic compositions are exemplified hereinbelow in Table 3.

TABLE 3

Flexural Modulus Physical Property

| Sample | Dry Flexural Modulus (MPa) | Wet Flexural Modulus (MPa) at 5 min. | Wet Flexural Modulus (MPa) at 15 min. | Wet Flexural Modulus (MPa) at 60 min. |
|---|---|---|---|---|
| PEO[1]/PEG[2]/Biomer 209H[6] (40/30/30 blend) | 700 | 290 | 140 | 40 |
| PEO[1]/PEG[2]/Bionolle 3001[5] (40/30/30 blend) | 540 | 180 | 140 | 30 |
| PEO[1]/PEG[2]/Bionolle 3001[5] (66/17/17 blend) | 450 | 190 | 150 | 50 |
| PEO[1]/PEG[2]/Eastar 14776[4] (40/30/30 blend) | 610 | 180 | 120 | 20 |
| PEO[1]/PEG[2]/BAK 404[3] (40/30/30 blend) | 720 | 210 | 100 | 40 |
| PEO[1]/PEG[2]/BAK 404[3] (40/40/20 blend) | 840 | 450 | 300 | 60 |
| PEO[1]/PEG[2]/BAK[3]/P-645[7] (36/27/27/10 blend) | 360 | 230 | 150 | 30 |
| PEO[1]/PEG[2]/BAK[3]/P-4141[8] (36/27/27/10 blend) | 350 | 220 | 120 | 40 |
| PEO[1]/PEG[2]/PLA 44D[9] (40/30/30 blend) | 1280 | 700 | 430 | 260 |
| PEO[1]/PEG[2]/PLA 62-50D[9] (40/30/30 blend) | 1220 | 660 | 450 | 220 |

The thermoplastic compositions also have physical properties of weight loss in water which can be determined by the percent weight loss of a dry specimen sample of a thermoplastic composition that has been submerged in water for time intervals of 5 minutes, 1 hour, 24 hours, and 1 week. For example, dry injection molded thermoplastic compositions having a thickness of about ⅛ inches are weighed to ascertain the dry specimens dry weight. The dry specimens are then soaked in water for a duration of 5 minutes, 1 hour, 24 hours, or 1 week, wherein dependent on the type of thermoplastic composition dissolution of the water-soaked specimen occurs. The water-soaked specimens are recovered for drying in a Blue M oven for 16 hours at 40° C. to obtain a final weight loss. The percent weight loss is calculated by subtracting the weight of dried water-soaked specimens minus the dry specimens initial weight, divided by the dry specimens initial weight, and multiplied by 100. The percent weight loss values of thermoplastic compositions described herein are exemplified hereinbelow in Table 4. A negative percent weight loss value is indicative of the thermoplastic composition being able to readily dissolve or disintegrate in water, and a positive percent weight loss value is indicative of the thermoplastic composition being able to maintain its structural integrity in water and not readily break apart into unrecognizable pieces. It has been found that the preferred thermoplastic compositions described herein can be molded into flushable tampon applicators of the present invention that exhibit a weight loss in water such that after being submerged for a period of 5 minutes the tampon applicators are capable or readily breaking apart, an observation of such tampon applicators being suitable for disposal by flushing down a toilet. These flushable tampon applicators exhibited a significant weight loss in water over a time period of 24 hours.

TABLE 4

% Weight (Wt.) Loss Physical Property

| Sample | % Wt. loss (5 min. soaking) | % Wt. loss (1 hour soaking) | % Wt. loss (24 hours soaking) | % Wt. loss (1 week soaking) |
| --- | --- | --- | --- | --- |
| $PEO^1/PEG^2$/Biomer $209H^6$ (40/30/30 blend) | −4 | −22 | −69 | −87 |
| $PEO^1/PEG^2$/Bionolle $3001^5$ (40/30/30 blend) | −8 | −16 | −63 | −67 |
| $PEO^1/PEG^2$/Bionolle $3001^5$ (66/17/17 blend) | −4 | −66 | −76 | −80 |
| $PEO^1/PEG^2$/Eastar $14776^4$ (40/30/30 blend) | −3 | −15 | −69 | −73 |
| $PEO^1/PEG^2$/BAK $404^3$ (40/30/30 blend) | −6 | −19 | −73 | −77 |
| $PEO^1/PEG^2$/BAK $404^3$ (40/40/20 blend) | −12 | −61 | −100 | −100 |
| $PEO^1/PEG^2/BAK^3$/P-$645^7$ (36/27/27/10 blend) | 6 | −22 | −61 | −67 |
| $PEO^1/PEG^2/BAK^3$/P-$4141^8$ (36/27/27/10 blend) | 1 | −18 | −60 | −65 |
| $PEO^1/PEG^2$/PLA $44D^9$ (40/30/30 blend) | 3 | −7 | −51 | −56 |
| $PEO^1/PEG^2$/PLA 62-$50D^9$ (40/30/30 blend) | 1 | −11 | −52 | −56 |

Optional Components

The flushable tampon applicators of the present invention can comprise optional ingredients in combination with the water-soluble and biodegradable components wherein the optional ingredients provide benefits to the final product or to the thermoplastic materials used in making the final product. Such benefits include, but are not limited to, stability including oxidative stability, brightness, flexibility, resiliency, toughness, workability, odor control, improved strength, improved modulus, improved melt flow characteristics, and/or distensibility of the thermoplastic compositions. The flushable tampon applicators typically comprise from about 0.05% to about 25% of optional ingredients by weight of the applicator. The optional ingredients include plasticizing agents, antioxidants, slip agents, optical brighteners, crystallization accelerators or retarders, flow promoters, processing aids, pigments or colorants, fillers, mold release agents, nucleating agents, coating agents, gelling agents, antistatic agents, dispersing agents, compatibilizers, lubricants, surfactants, heat stabilizers, odor masking agents, opacifying agents such as titanium dioxide and aluminum oxide, dyes, viscosity modifiers, and mixtures thereof. The optional plasticizing agents, coating agents, fillers, and viscosity modifiers are described in detail hereinbelow.

Optional Plasticizing Agent

If a plasticizing agent is included with thermoplastic polymers for making the flushable tampon applicators of the present invention, the plasticizer is included at concentrations ranging from about 1% to about 25% by weight of the applicator. In this context, the term "plasticizing agent" refers to any organic compound that, when added to a thermoplastic polymer, can provide modification to the polymer's morphology to result in increased ease of processing of the polymer and increased toughness and flexibility of the polymer after processing. Examples of optional plasticizing agents include glycerin, glycerin derivatives such as triacetin and glycerol monostearate, sorbitol, erythritol, glucidol, mannitol, sucrose, ethylene glycol, propylene glycol, diethylene glycol, triethylene glycol, diethylene glycol dibenzoate, dipropylene glycol dibenzoate, triethylene glycol caprate-caprylate, butylene glycol, pentamethylene glycol, hexamethylene glycol, diisobutyl adipate, oleic amide, erucic amide, palmitic amide, dimethyl acetamide, dimethyl sulfoxide, methyl pyrrolidone, tetramethylene sulfone, oxa monoacids, oxa diacids, polyoxa diacids, diglycolic acids, triethyl citrate, acetyl triethyl citrate, tri-n-butyl citrate, acetyl tri-n-butyl citrate, acetyl tri-n-hexyl citrate, alkyl lactates, phthalate polyesters excluding the aromatic terephthalate polyesters suitable for use as a biodegradable polymer herein, adipate polyesters, glutate polyesters, diisononyl phthalate, diisodecyl phthalate, dihexyl phthalate, alkyl alylether diester adipate, dibutoxyethoxyethyl adipate, and mixtures thereof. Examples of commercially available plasticizers include the adipate polyester sold under the Plasthall 645 tradename and triethylene glycol caprate-caprylate sold under the Plasthall 4141 tradename, both of which are available from the C. P. Hall Corporation.

Optional Coating Agent

The flushable tampon applicators of the present invention preferably comprise from about 0.05% to about 10% of a coating agent by weight of the applicator. The coating agent provides stability to the final applicator product by serving as a moisture barrier, and is considered to be effective in reducing or eliminating the sticky or slippery film feel that can occur when the applicator comes in contact with air-laden or human moisture. The coating agent can be applied using any suitable coating technique known in the art for effectively applying a coating material on the outer or exterior surface of a thermoplastic material used to form a flushable tampon applicator. Some known effective coating methods can be typically described as tumbling coating, spray coating, brushing, dip coating, slot coating, gravure coating, extrusion coating, co-extrusion coating, and the like.

While the coating material can be applied directly to the outer or exterior surface of a thermoplastic material described herein, the coating material can also be applied as a coating solution. The coating solution comprises the coating solubilized in a volatile solvent, wherein suitable volatile solvents include saturated and unsaturated hydrocarbons such as heptane, cyclohexane, and toluene; halogenated hydrocarbons such as chlorobenzene, chloroform, and methylene chloride; hydrocarbon alcohol ethers; and mixtures thereof.

Optional preferred coating agents suitable for use herein include waxes, hydrogenated vegetable oils, food grade shellac, epoxy resins, vinylidene chloride copolymer latexes, polysiloxanes, sucrose fatty acid esters, and mixtures thereof. A specific example of a vinylidene chloride copolymer latex is Daran SL 143 which is commercially available from the Hampshire Chemical Corporation.

Specific nonlimiting examples of waxes suitable for use as an optional preferred coating agent include animal waxes (e.g., beeswax, spermaceti, lanolin, and shellac wax); vegetable waxes (e.g., carnauba, candelilla, bayberry, and sugar cane); mineral waxes (e.g., fossil or earth waxes such as ozokerite, ceresin, and montan, or petroleum waxes such as paraffin, microcrystalline, petrolatum, slack and scale wax); chlorinated naphthalenes (e.g., "Halowax"); and mixtures thereof.

Optional Fillers

The flushable tampon applicators of the present invention can optionally comprise fillers which can aid in the applicators having an opaque appearance, in addition to providing the applicators with a smooth, soft texture and improved water-dispersibility. The optional fillers can be added by compounding the fillers with the thermoplastic polymers and any other optional ingredient described herein, and processing this compounded mixture according to the disclosed methods of constructing flushable tampon applicators of the present invention. Suitable optional fillers include inorganic and organic filler materials. Nonlimiting examples of suitable inorganic fillers include clays, silica, mica, wollastonite, calcium hydroxide, calcium carbonate, sodium carbonate, magnesium carbonate, barium sulfate, magnesium sulfate, kaolin, calcium oxide, magnesium oxide, aluminum hydroxide, magnesium silicates including talc, and mixtures thereof. Nonlimiting examples of suitable organic fillers include wood flour, walnut shell flour, alpha cellulose floc, cellulose fibers, chitin, chitosan powders, organosilicone powders, natural starches, vegetable starches, and mixtures thereof. The optional fillers are typically included at concentrations ranging from about 0.5% to about 10% by weight of the applicator.

Optional Viscosity Modifiers

The flushable tampon applicators of the present invention can optionally comprise viscosity modifiers to increase the viscosity of the water-dispersible and biodegradable thermoplastic polymers described herein so that they can be molded using a preferred injection molding or any other molding technique described herein. Such viscosity modifiers are typically included at concentrations ranging from about 0.1% to about 5%, preferably from about 0.1% to about 2% by weight of the applicator. Nonlimitng examples of suitable viscosity modifiers include trifunctional alcohols such as trimethylolpropane, tetrafunctional alcohols such as pentaerythritol, trifunctional carboxylic acids such as citric acid, and the like.

Method of Manufacture

The flushable tampon applicators of the present invention may be prepared by any known or otherwise effective technique for providing a disposable tampon applicator provided that the article is made to contain water-dispersible and biodegradable materials described herein, preferably a blend of water-dispersible and biodegradable materials. Typically, the flushable tampon applicators are molded in a desired shape or configuration using a variety of molding techniques to provide a thermoplastic applicator comprising an outer tubular member and a plunger. Such molding techniques include injection molding, extrusion molding, blow molding, compression molding, and cast film. These molding techniques can be used alone or in combination to make the flushable tampon applicators of the present invention. For example, the outer tubular member and plunger components of the flushable tampon applicators herein can be made using an injection molding apparatus, or the outer tubular member and plunger can be made using an extrusion molding apparatus, or the outer tubular member can be made using injection molding and the plunger made using extrusion molding, or the outer tubular member made by extrusion molding and the plunger made by injection molding, or the outer tubular member and/or plunger are made using a combination of extrusion and injection molding.

Generally, the process of making flushable tampon applicators of the present invention involves charging one or more high molecular weight polyethylene oxides, one or more low molecular weight polyethylene glycols, one or more aliphatic polyesteramides, and any optional ingredients such as a plasticizer into an injection molding apparatus, and molding the melt blended mixture into the desired flushable tampon applicator. Alternatively, a blend of the thermoplastic materials and optional plasticizer can be compounded into pellets by means of an extruder, and the pellets are then constructed into flushable tampon applicators using an injection molding apparatus.

One example of a procedure of making flushable tampon applicators of the present invention involves mixing the thermoplastic polymers and optional plasticizer in a variable speed, high intensity blender, extruding the mixture at a temperature above the melting temperature of the thermoplastic polymers to form a rod, chopping the rod into pellets, and injection molding the pellets into the desired flushable tampon applicator form.

The extruders which are commonly used to melt process thermoplastic compositions into compounded pellets are generally single-screw extruders, twin-screw extruders, and kneader extruders. Examples of commercially available extruders suitable for use herein include the Black-Clawson single-screw extruders, the Werner and Pfleiderer co-rotating twin-screw extruders, the HAAKE Polylab System counter-rotating twin screw extruders, and the Buss kneader extruders. A typical extrusion process can be described as compounding blended components using a twin-screw extruder having a screw diameter of 30 mm, a feed section, and a die tip. The blend is compounded at about 100 revolutions per minute (rpm) at a temperature ranging from about 60° C. at the feed section to about 130° C. at the die tip. The final product is a compounded rod that is chopped into pellets suitable for molding into desired flushable tampon applicators using an injection molding apparatus. General discussions of extrusion molding are disclosed in the *Encyclopedia of Polymer Science and Engineering*; Volume 6, pp. 571–31, 1986, and Volume 11, pp. 262–285, 1988; John Wiley and Sons, New York; which disclosures are incorporated by reference herein.

Injection molding is the most commonly used process for constructing and configuring tampon applicators into a desired shape of form. This process is typically carried out under controlled temperature, time, speed and pressure, and involves melt processing pellets or blends of thermoplastic compositions wherein the melted thermoplastic composition is injected into a mold, cooled, and molded into a desired plastic object.

An example of a suitable injection molding machine is the Engel Tiebarless ES 60 TL apparatus having a mold, a nozzle, and a barrel that is divided into zones wherein each zone is equipped with thermocouples and temperature-control units. The zones of the injection molding machine can be described as front, center, and rear zones whereby the pellets are introduced into the front zone under controlled temperature. The temperature of the nozzle, mold, and barrel components of the injection molding machine can vary according to the melt processing temperature of the pellets and the molds used, but will typically be in the following ranges:

| Component | Temp (° C.) |
| --- | --- |
| Nozzle | 135–230 |
| Front Zone | 70–200 |

| Component | Temp (° C.) |
|---|---|
| Center Zone | 100–225 |
| Rear Zone | 120–225 |
| Mold | 20–50 |

Other typical processing conditions include an injection pressure of from about 300 pounds per square inch (psi) to about 1600 psi (about 2100 KPa to about 11,200 KPa), a holding pressure of about 400 psi to about 1300 psi (about 2800 KPa to about 9100 KPa), a hold time of about 2 seconds to about 15 seconds, and an injection speed of from about 0.98 inches per second (in/sec) to about 8 in/sec.

Other suitable injection molding apparatus are the injection molding machines made by Battenfeld, Brabender, Killion, Demag and Arburg, Windsor, Hesas, Boy, Van Dorn, Engel, and the Fischer companies. Specific examples of other suitable injection molding machines include the Van Dorn Model 150-RS-8F, the Battenfeld Model 1600, and the Engel Model ES80. A general discussion of injection molding is disclosed in the *Encyclopedia of Polymer Science and Engineering*, Volume 8, pp. 102–138, John Wiley and Sons, New York, 1987, which disclosure is incorporated by reference herein.

The flushable tampon applicators of the present invention are generally made using the extrusion and injection molding techniques described hereinabove. These techniques involve melt processing the thermoplastic polymers and any optional ingredients wherein the thermoplastic polymers and optional ingredients have melting temperatures typically ranging from about 25° C. to about 350° C., more typically from about 40° C. to about 300° C., even more typically from about 50° C. to about 200° C. Therefor the thermoplastic polymers suitable for use in making the flushable tampon applicators of the present invention desirably have individual melt flow rates of from about 0.1 gram/10 minutes to about 600 grams/10 minutes, preferably from about 1 gram/10 minutes to about 400 grams/10 minutes, more preferably from about 5 grams/10 minutes to about 200 grams/10 minutes, even more preferably from about 10 grams/10 minutes to about 150 grams/10 minutes, as determined according to the ASTM Test Method D1238-E.

The final products of flushable tampon applicators of the present invention are packaged in moisture-proof wrappers for storage prior to use. The moisture-proof wrappers prevents moisture from contacting the applicator or tampon pledget, and therefore assures shelf-stability for the tampon and provides an asethetically pleasing and acceptable tampon product prior to actual use. The flushable tampon applicators of the present invention can be packaged in any suitable wrapper provided that the wrapper is soil proof and disposable with dry waste. Preferred wrappers are those made from biodegradable materials which create minimal or no environmental concerns for their disposal. It is contemplated, however, that the tampon applicators of the present invention can be packaged in flushable wrappers made from paper, nonwoven, cellulose, thermoplastic, or any other suitable flushable material, or combinations of these materials.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified concentrations are weight-weight percents, unless otherwise specified.

Example 1

Flushable tampon applicators of the present invention are made by a melt extrusion process of blending water-dispersible polymers and biodegradable polymers using a Werner Pfleiderer ZSK-30 co-rotating twin screw extruder having a screw diameter of 30 mm, six heating zones, a two hole die plate, and two feeding hoppers. A dry blend mixture of water-dispersible polymers such as high molecular weight polyethylene oxide commercially available as POLYOX® WSR-80 and low molecular weight polyethylene glycol commercially available as PEG-8000 is prepared. The water-dispersible polymer dry blend mixture is fed into one feeding hopper while a biodegradable polymer is fed into the other feeding hopper. The water-dispersible polymer dry blend mixture and biodegradable polymer are then melt blended upon entering the heating zones of the extruder. Next, the die is used to extrude the melt blended mixture of water-dispersible polymer and biodegradable polymer into rods that are air-cooled and pelletized for injection molding into a desired flushable tampon applicator. Optionally, a plasticizer can be included in this process of making flushable tampon applicators of the present invention. If a plasticizer is included, the plasticizer is mixed with the pellets and this plasticizer/pellet mixture is soaked for two days prior to injection molding. The water-dispersible polymers, suitable biodegradable polymer, and extrusion settings are further described hereinbelow in Table 5 and Table 6.

TABLE 5

Extrusion Molded Thermoplastic Compositions

| Extruder Settings | PEO[1]/<br>PEG[2]/<br>BAK 404[3]<br>(40/30/30<br>blend) | PEO[1]/<br>PEG[2]/<br>BAK 404[3]<br>(40/40/20<br>blend) | PEO[1]/<br>PEG[2]/<br>Eastar<br>14776[4]<br>(40/30/30<br>blend) | PEO[1]/<br>PEG[2]/<br>Bionolle<br>3001[5]<br>(66/17/17<br>blend) |
|---|---|---|---|---|
| Zone 1 (° C.) | Off | 60 | Off | 60 |
| Zone 2 (° C.) | 80 | 70 | 80 | 70 |
| Zone 3 (° C.) | 101 | 110 | 99 | 110 |
| Zone 4 (° C.) | 128 | 118 | 130 | 113 |
| Zone 5 (° C.) | 141 | 122 | 140 | 122 |
| Zone 6 (° C.) | 114 | 103 | 115 | 109 |
| Die (° C.) | 120 | 105 | 120 | 103 |
| Screw Speed (rpm) | 100 | 250 | 100 | 300 | rpm—revolutions per minute
[1]polyethylene oxide available as POLYOX ® WSR-80 from the Union Carbide Corporation
[2]polyethylene glycol available as PEG-8000 from Union Carbide
[3]aliphatic polyesteramide available as BAK 404 from Bayer Aktiengesellschaft
[4]aliphatic-aromatic copolyester available as Eastar Biodegradable Copolyester 14776 from Eastman Chemical
[5]diacid-diol aliphatic polyester available as BIONOLLE 3001 from the Showa Highpolymer Company, Ltd.

TABLE 6

Extrusion Molded Thermoplastic Compositions

| | PEO[1]/<br>PEG[2]/<br>Bionolle | PEO[1]/<br>PEG[2]/<br>Biomer | PEO[1]/<br>PEG[2]/<br>BAK<br>404[3]/ | PEO[1]/<br>PEG[2]/<br>BAK<br>404[3]/ |
|---|---|---|---|---|

| Extruder Settings | 3001[5] (40/30/30 blend) | 209H[6] (40/30/30 blend) | P-645[7] (36/27/27/10 blend) | P-4141[8] (36/27/27/10 blend) |
|---|---|---|---|---|
| Zone 1 (° C.) | Off | 75 | Off | Off |
| Zone 2 (° C.) | 50 | 85 | 80 | 80 |
| Zone 3 (° C.) | 125 | 98 | 101 | 101 |
| Zone 4 (° C.) | 130 | 146 | 128 | 128 |
| Zone 5 (° C.) | 145 | 161 | 141 | 141 |
| Zone 6 (° C.) | 125 | 148 | 114 | 114 |
| Die (° C.) | 116 | 130 | 120 | 120 |
| Screw Speed (rpm) | 100 | 300 | 100 | 100 |

[6]polyhydroxyalkanoate available as Biomer 209H from Biomer Frost-Kasten-Str., Krailling, Germany
[7]adipate polyester plasticizer available as Plasthall 645 from C. P. Hall
[8]triethylene glycol caprate-caprylate plasticizer available as Plasthall 4141 from C. P. Hall Example 2

Flushable tampon applicators of the present invention are made by dry blending a mixture of water-dispersible and biodegradable polymers, and then feeding this dry blended mixture of polymers into a HAAKE Polylab System counter-rotating twin screw extruder. The extruder is equipped with a single hole die plate for compounding the dry blended mixture into a single strand of molten plastic that is air-cooled and then chopped into small discs having a diameter of 20 mm and a thickness of 0.5 mm. The small discs are grounded using an IMS LP-288SC Grinder for injection molding into a desired flushable tampon applicator. The dry blended thermoplastic compositions of water-dispersible polymers and biodegradable polymers, in addition to the extrusion apparatus settings, are described hereinbelow in Table 7.

TABLE 7

Extrusion Molded Thermoplastic Compositions

| Extruder Settings | PEO[1]/PEG[2]/PLA 44D[9] (40/30/30 blend) | PEO[1]/PEG[2]/PLA 62-50D[9] (40/30/30 blend) |
|---|---|---|
| Zone 1 (° C.) | 80 | 80 |
| Zone 2 (° C.) | 200 | 200 |
| Zone 3 (° C.) | 210 | 210 |
| Die (° C.) | 130 | 120 |
| Screw Speed (rpm) | 30 | 25 |

[9]polylactic acids available as PLA 44D grade and PLA 62-50D grade from Cargill-Dow Polymers, LLC Injection Molding An Engel Tiebarless ES 60 TL injection molding machine is suitable for manufacturing the final product of thermoplastic pellets of Examples 1 and 2 into flushable tampon applicators of the present invention. The injection molding process involves using a 25 mm screw and controlled processing conditions of controlled temperature, time, speed, and pressure, wherein the pellets are melt processed, injected into a mold, cooled, and then molded into the desired flushable tampon applicator.

The Engel injection molding machine is also suitable for manufacturing composite paper flushable tampon applicators. Typically, spiral-wound paper is formed into paper tubes having a length of about 35 mm, inside diameter of about 10.8 mm, outside diameter of about 11.2 mm, and a weight of about 0.25 grams. The paper tube is positioned over a mold core pin, the mold is clamped shut, and a thermoplastic composition is injected into the mold. The paper tube is positioned over the mold core pin such that the thermoplastic composition is melt processed to flow over the entire length of the outer surface of the paper tube. Therefore, the resultant composite paper tampon applicator comprises a paper inner surface, thermoplastic resin outer surface, and thermoplastic petals and grip components.

Examples of thermoplastic compositions and injection molding settings are described hereinbelow in Table 8, Table 9, and Table 10.

TABLE 8

Injection Molded Thermoplastic Compositions

| Injection Molding Settings | PEO[1]/PEG[2]/BAK 404[3] (40/30/30 blend) | PEO[1]/PEG[2]/BAK 404[3] (40/40/20 blend) | PEO[1]/PEG[2]/Eastar 14776[4] (40/30/30 blend) | PEO/PEG/Bionolle 3001[5] (66/17/17 blend) |
|---|---|---|---|---|
| Nozzle (° C.) | 177 | 163 | 149 | 135 |
| Zone 1 (° C.) | 149 | 107 | 127 | 74 |
| Zone 2 (° C.) | 160 | 135 | 138 | 107 |
| Zone 3 (° C.) | 168 | 149 | 143 | 121 |
| Mold (° C.) | 21 | 21 | 21 | 21 |
| Screw Speed (rpm) | 120 | 192 | 120 | 192 |
| Injection Speed (in/sec) | 4 | 4 | 4 | 4 |
| Injection Pressure (psi) | 843 | 418 | 1562 | 1302 |
| Hold Time (sec) | 4 | 12 | 8 | 5 |
| Hold Pressure (psi) | 500 | 800 | 650 | 1250 |
| Cool Time (sec) | 30 | 30 | 25 | 30 | psi - pounds per square inch
in/sec - inches per second
sec - seconds

TABLE 9

Injection Molded Thermoplastic Compositions

| Injection Molding Settings | PEO[1]/PEG[2]/Bionolle 3001[5] (40/30/30 blend) | PEO[1]/PEG[2]/Biomer 209H[6] (40/30/30 blend) | PEO[1]/PEG[2]/BAK 404[3]/P-645[7] (36/27/27/10 blend) | PEO[1]/PEG[2]/BAK 404[3]/P-4141[8] (36/27/27/10 blend) |
|---|---|---|---|---|
| Nozzle (° C.) | 221 | 149 | 149 | 149 |
| Zone 1 (° C.) | 193 | 65 | 65 | 65 |
| Zone 2 (° C.) | 216 | 79 | 79 | 79 |
| Zone 3 (° C.) | 216 | 143 | 121 | 121 |
| Mold (° C.) | 21 | 21 | 21 | 21 |
| Screw Speed (rpm) | 120 | 192 | 192 | 192 |
| Injection Speed (in/sec) | 4 | 4 | 4 | 4 |
| Injection Pressure (psi) | 641 | 388 | 405 | 564 |
| Hold Time (sec) | 4 | 15 | 8 | 8 |
| Hold Pressure (psi) | 1100 | 500 | 500 | 500 |
| Cool Time (sec) | 35 | 60 | 40 | 40 |

TABLE 10

Injection Molded Thermoplastic Compositions

| Injection Molding Settings | PEO[1]/PEG[2]/PLA 44D[9] (40/30/30 blend) | PEO[1]/PEG[2]/PLA 62-50D[9] (40/30/30 blend) | Composite Paper with 40/30/30 blend of PEO[1]/PEG[2]/BAK 404[3] |
|---|---|---|---|
| Nozzle (° C.) | 199 | 199 | 163 |
| Zone 1 (° C.) | 149 | 149 | 121 |
| Zone 2 (° C.) | 149 | 149 | 140 |
| Zone 3 (° C.) | 177 | 177 | 152 |
| Mold (° C.) | 32 | 32 | 24 |
| Screw Speed (rpm) | 120 | 120 | 160 |
| Injection Speed (in/sec) | 4 | 4 | 3 |
| Injection Pressure (psi) | 348 | 315 | 400 |

TABLE 10-continued

Injection Molded Thermoplastic Compositions

| Injection Molding Settings | PEO[1]/PEG[2]/ PLA 44D[9] (40/30/30 blend) | PEO[1]/PEG[2]/ PLA 62-50D[9] (40/30/30 blend) | Composite Paper with 40/30/30 blend of PEO[1]/ PEG[2]/ BAK 404[3] |
|---|---|---|---|
| Hold Time (sec) | 5 | 5 | 5 |
| Hold Pressure (psi) | 800 | 800 | 300 |
| Cool Time (sec) | 30 | 30 | 4 |

What is claimed is:

1. A flushable applicator comprising:
   (a) from about 1% to about 90% by weight of polyethylene oxides having a weight average molecular weight of from about 65,000 daltons to about 8,000,000 daltons;
   (b) from about 1% to about 40% by weight of polyethylene glycols having a number average molecular weight of from about 500 daltons to about 20,000 daltons; and
   (c) from about 9% to about 59% by weight of an aliphatic polyesteramide.

2. A flushable tampon applicator of claim 1 wherein the polyethylene oxides have a weight average molecular weight of from about 80,000 daltons to about 2,000,000 daltons.

3. A flushable tampon applicator of claim 1 wherein the polyethylene glycols have a number average molecular weight of from about 550 daltons to about 15,000 daltons.

4. A flushable tampon applicator of claim 1 wherein the aliphatic polyesteramide has a weight average molecular weight of from about 10,000 daltons to about 500,000 daltons.

5. A flushable tampon applicator of claim 1 wherein the applicator further comprises a coating agent selected from the group consisting of waxes, hydrogenated vegetable oils, food grade shellac, epoxy resins, vinylidene chloride copolymer latexes, polysiloxanes, and mixtures thereof.

6. A flushable tampon applicator of claim 1 wherein the applicator further comprises a plasticizer selected from the group consisting of glycerin, triacetin, glycerol, monostearate, sorbitol, erythritol, glucidol, mannitol, sucrose, ethylene glycol, polyethylene glycol, diethylene glycol, triethylene glycol, diethylene glycol dibenzoate, dipropylene glycol dibenzoate, triethylene glycol caprate-caprylate, butylenes glycol, pentamethylene glycol, hexamethylene glycol, diisobutyl adipate, oleic amide, erucic amide, palmitic amide, dimethyl acetamide, dimethyl sulfoxide, methyl pyrrolidine, tetramethylene sulfone, oxa monoacids, oxa diacids, polyoxa diacids, diglycolic acids, trimethyl citrate, acetyl triethyl citrate, tri-n-butyl citrate, acetyl tri-n-butyl citrate, acetyl tri-n-hexyl citrate, alkyl lactates, phthalate polyesters, adipate polyesters, glutate polyesters, diisononyl phthalate, diisodecyl phthalate, dihexyl phthate, alkyl alylether diester adipate, dibutoxyethoxyethyl adipate, and mixture thereof.

7. A thermoplastic composition comprising:
   (a) from about 1% to about 90% by weight of polyethylene oxides having a weight average molecular weight of from about 65,000 daltons to about 8,000,000 daltons;
   (b) from about 1% to about 40% by weight of polyethylene glycols having a number average molecular weight of from about 500 daltons to about 20,000 daltons; and
   (c) from about 9% to about 59% by weight of an aliphatic polyesteramide.

8. A thermoplastic composition of claim 7 wherein the polyethylene oxides have a weight average molecular weight of from about 80,000 daltons to about 2,000,000 daltons.

9. A thermoplastic composition of claim 7 wherein the polyethylene glycols have a number average molecular weight of from about 550 daltons to about 15,000 daltons.

10. A thermoplastic composition of claim 7 wherein the composition further comprises a plasticizer selected from the group consisting of glycerin, triacetin, glycerol, monostearate, sorbitol, erythritol, glucidol, mannitol, sucrose, ethylene glycol, polyethylene glycol, diethylene glycol, triethylene glycol, diethylene glycol dibenzoate, dipropylene glycol dibenzoate, triethylene glycol caprate-caprylate, butylenes glycol, pentamethylene glycol, hexamethylene glycol, diisobutyl adipate, oleic amide, erucic amide, palmitic amide, dimethyl acetamide, dimethyl sulfoxide, methyl pyrrolidine, tetramethylene sulfone, oxa monoacids, oxa diacids, polyoxa diacids, diglycolic acids, trimethyl citrate, acetyl triethyl citrate, tri-n-butyl citrate, acetyl tri-n-butyl citrate, acetyl tri-n-hexyl citrate, alkyl lactates, phthalate polyesters, adipate polyesters, glutate polyesters, diisononyl phthalate, diisodecyl phthalate, dihexyl phthate, alkyl alylether diester adipate, dibutoxyethoxyethyl adipate, and mixture thereof.

11. A method of making a flushable tampon applicator wherein the method comprises the steps of:
   (a) preparing a blended thermoplastic composition comprising:
      i. from about 1% to about 90% by weight of polyethylene oxides having a weight average molecular weight of from about 65,000 daltons to about 8,000,000 daltons;
      ii. from about 1% to about 40% by weight of polyethylene glycols having a number average molecular weight of from about 500 daltons to about 20,000 daltons; and
      iii. from about 9% to about 59% by weight of an aliphatic polyesteramide,
   (b) injection molding the blended thermoplastic composition into molded thermoplastic components used to construct the flushable tampon applicator.

12. A method of claim 11 wherein the polyethylene oxides have a weight average molecular weight of from about 80 000 daltons to about 2,000,000 daltons.

13. A method of claim 11 wherein the polyethylene glycols have a number average molecular weight of from about 550 daltons to about 15,000 daltons.

* * * * *